United States Patent [19]

Matsuo et al.

[11] 4,420,560

[45] Dec. 13, 1983

[54] METHOD FOR MODIFICATION OF FATS AND OILS

[75] Inventors: Takaharu Matsuo, Sennan; Norio Sawamura, Osaka; Yukio Hashimoto, Kishiwada; Wataru Hashida, Osaka, all of Japan

[73] Assignee: Fuji Oil Company, Limited, Japan

[21] Appl. No.: 322,248

[22] Filed: Nov. 17, 1981

[51] Int. Cl.$^3$ .............................................. C12P 7/64
[52] U.S. Cl. .................................... 435/134; 435/271; 426/33
[58] Field of Search ................ 435/134, 135, 162, 271

[56] References Cited

U.S. PATENT DOCUMENTS 3,190,753  6/1965  Claus et al. ................... 435/134 X
4,268,527  5/1981  Matsuo et al. ................. 435/134 X
4,275,011  6/1981  Tanaka et al. .................. 435/134 X
4,275,081  6/1981  Coleman et al. ............... 435/134 X Primary Examiner—Robert A. Yoncoskie
Attorney, Agent, or Firm—Wenderoth, Lind & Ponack

[57] ABSTRACT

In a method of the modification of a fat or oil wherein a mixture (mixture A) containing a glyceride-type fat or oil to be modified (material A) and a fatty acid or a nonglyceride-type ester thereof (material B) is selectively transesterified in the presence of a catalyst having a selective transesterification activity (catalyst A); the resulting fat or oil (resultant A), fatty acid or nonglyceride-type ester thereof (resultant B) and catalyst are recovered from the reaction mixture; and then a hard butter is produced from the resultant A, the improvement comprises hydrogenating a part or all of the resultant B and reusing the hydrogenated product as a part of the mixture A.

10 Claims, 1 Drawing Figure

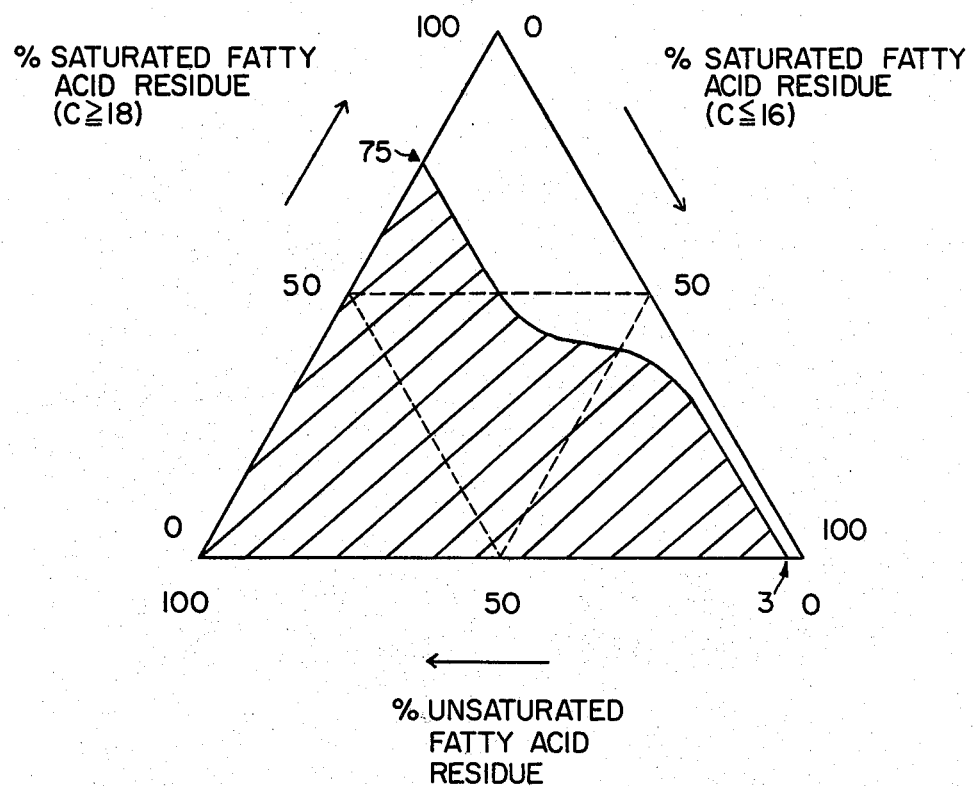

METHOD FOR MODIFICATION OF FATS AND OILS

The present invention relates to a method for the modification of fats and oils. More particularly, according to the method of the present invention, fats and oils are modified by transesterification to give fats and oils suitable for a hard butter such as a cacao butter substitute.

Transesterification is one of the fundamental techniques for modifying fats and oils and it has been known that transesterification can be carried out by using a metallic catalyst such as an alkaline metal or the like.

Recently, it has been proposed that transesterification can be carried out by using a lipolytic enzyme. According to this enzymatic transesterification, a selective transesterification reaction which has not been expected in the transesterification using a metallic catalyst can be effected and a fatty acid residue at a specific position of a glyceride can be readily interchanged with another appropriate fatty acid residue. Therefore, the enzymatic transesterification makes possible to apply the modification of fats and oils for various purposes. Further, although hydrolysis of fats and oils also occurs in the enzymatic transesterification, techniques for reducing the formation of hydrolyzates, particularly, diglycerides to a large extent such as not more than several percent have been developed (for example, U.S. Pat. No. 4,268,527) and hence, the practical value of the enzymatic transesterification in the production of a hard butter has increased.

In general, the enzymatic transesterification is carried out by reacting a fat or oil to be modified with an appropriate fatty acid source such as a fatty acid or a nonglyceride-type ester thereof in the presence of a lipolytic enzyme to selectively interchange a fatty acid residue at a specific position of the fat or oil with that of the fatty acid source, removing the enzyme and then recovering the resulting transesterified fat or oil from the reaction mixture.

However, a selective transesterification reaction is to randomize or unify the distribution of fatty acid residues among reaction sites of reactants. Therefore, when the difference in fatty acid components at a reaction site between a fat or oil to be modified and a desired fat or oil becomes greater, a larger amount of a fatty acid source is needed. Further, it is difficult to reuse a fatty acid fraction or ester thereof present in a reaction mixture after separation of a desired fat or oil as a fatty acid source since the fatty acid composition thereof is quite different from that of the fatty acid source initially used and hence, a large amount of the fatty acid source is also needed.

Moreover, as mentioned above, hydrolysis of a fat or oil occurs in the enzymatic tranesterification and it causes lowering of yield and deterioration of quality of the desired glyceride due to miscibility thereof with hydrolyzates. Although this problem can be solved by carrying out the selective transesterification reaction in a dry reaction system, it still presents the need for a shorter reaction time of transesterification.

Under these circumstances, the present inventors have intensively studied the application of a selective transesterification in the production of a hard butter and have found that when a fatty acid or an ester thereof in a reaction mixture is recovered after the selective transesterification reaction, hydrogenated and then used again as all or a part of a fatty acid source, it is possible to decrease the amount of the fatty acid source to be used, to improve yield and quality of the desired hard butter product and to shorten the reaction time.

The main object of the present invention is to provide a method for the modification of fats and oils which is useful in the production of a hard butter. This object as well as other objects and advantages of the present invention will become apparent to those skilled in the art from the following description and the accompanying drawing wherein FIG. 1 is a triangle showing a fatty acid composition at the $\alpha$-position (1 and 3-positions) of a fat oil to be modified in the present invention.

In brief, the present invention provides an improvement in a method for the modification of a fat or oil wherein a mixture (hereinafter referred to as mixture A) containing a fat or oil to be modified (hereinafter referred to as material A) and a fatty acid or a nonglyceride-type ester thereof (hereinafter referred to as material B) is selectively tranesterified in the presence of a catalyst having a selective transesterification activity (hereinafter referred to as catalyst A); the resulting fat or oil (hereinafter referred to as resultant A), fatty acid or nonglyceride-type ester thereof (hereinafter referred to as resultant B) and catalyst (hereinafter referred to as catalyst B) are recovered from the reaction mixture; and then a hard butter is produced from the resultant A. The improvement comprises hydrogenating a part or all of the resultant B and reusing the hydrogenated product (hereinafter referred to as material C) as a part of the mixture A. Further, in the method of the present invention, all or a low melting point fraction of the resultant A may be also reused as a part of the mixture A, and/or a fatty acid having not more than 16 carbon atoms or an ester thereof may be removed from the resultant B or the material C.

The material A used in the method of the present invention is a glyceride-type fat or oil and, preferably, rich in oleic acid residue at the $\beta$-position (2-position) thereof. More particularly, the fatty acid residues at the $\beta$-position of the material A are preferably composed of not less than 70% of oleic acid residue. When the amount of oleic acid residue at the $\beta$-position is too small, it is difficult to obtain a hard butter suitable for a cacao butter substitute, which is rich in oleic acid residue at the $\beta$-position, in good yield even if a selective tranesterification at the $\beta$-position is effected. It is preferable that the fatty acid residues at the $\beta$-position of the material A consist essentially of those derived from a fatty acid having 14 to 22 carbon atoms. More particularly, the fatty acid residue composition of the $\beta$-position is preferably that within the shaded part of FIG. 1. In FIG. 1, each top point of the triangle shows that the fatty acid residue composition is composed of 100% of the residues derived from a saturated fatty acid having not less than 18 carbon atoms (e.g. stearic acid, arachic acid, behenic acid, in general, mainly stearic acid), 100% of the residues derived from a saturated fatty acid having not more than 16 carbon atoms (e.g. palmitic acid, myristic acid, in general, mainly palmitic acid), or 100% of the residues derived from an unsaturated fatty acid (in general, mainly an unsaturated fatty acid having 18 carbon atoms such as oleic acid, linoleic acid, linolenic acid, etc.), respectively. Within the shaded part, when the amount of the residues derived from an unsaturated fatty acid is greater, the more desirable effects can be obtained by hydrogenating the resultant B and reusing it as a part of the mixture A. Examples of the material A are olive oil, oleic safflower oil, camellia oil, palm oil, rapeseed oil (Zero Erucic type), shea butter, sal fat, mango fat, kokum butter, Borneo tallow, Malabar tallow and a fractionated fat thereof. However, in the case of such a highly fractionated fat as the fatty acid residue composition thereof is beyond the shaded part of FIG. 1, for example, when a fat to be modified contains more than 80% of 2-oleo-1,3-distearin (hereinafter referred to as SOS) or more than 98% of 2-oleo-1,3-dipalmitin (hereinafter referred to as POP), the effect of the method of the present invention is decreased.

The material B is a fatty acid source and, preferably, contains the residue of palmitic acid or stearic acid. In general, the fatty acid residues in the material B are composed of not less than 50% of palmitic and stearic acid residues and palmitic acid residue is at most 1.5 times as much as stearic acid residue by weight. The material B may be in the form of a free fatty acid or an ester thereof. The ester should be separable from a triglyceride, that is, it should be a nonglyceride-type ester since, if the ester is, for example, a diglyceride, which forms an eutectic mixture with a triglyceride and is hardly separated from the triglyceride by a conventional industrial operation, it remains in a hard butter product which results in deterioration of quality of the product. Examples of the nonglyceride-type ester are monohydric alcohol esters, dihydric alcohol esters such as propylene glycol esters, sorbitan esters and the like. In the present invention, since the content of the resultant B in the reaction mixture is higher than that of fatty acids in a conventional fat or oil to be subjected to refining, separation of the resultant A from the resultant B is readily effected when the resultant B is a monohydric alcohol ester rather than a free fatty acid. Therefore, the material B is preferably a fatty acid monohydric alcohol ester, particularly, the alcohol moiety thereof has 1 to 4 carbon atoms. Further, when the method of the present invention includes a step for fractionating different fatty acid esters as mentioned hereinafter, it is preferable to use a fatty acid monohydric alcohol ester as the material B since the fractionation can be readily carried out.

The mixture A containing the materials A and B may further contain a solvent such as n-hexane so as to form a liquid phase. When the water content of the mixture A is high, hydrolysis occurs simultaneously with the tranesterification reaction. That is, the formation of a diglyceride which can hardly be separated from the desired triglyceride is increased and thereby, the resultant A can hardly be used in the production of a hard butter wherein a solid fat index (SFI) curve and a cooling curve of the resultant A and a tempering operation are of importance. Therefore, it is preferable to carry out the transesterification reaction in as dry a state as possible and water content of the transesterification reaction system, including that of the solvent to be used and the catalyst, is preferably not more than 0.18% by weight based on the total amount of the materials A and B.

The catalyst A to be used in the present invention shows a superior activity in a dry reaction system without addition of water as mentioned above. A typical example of the catalyst A is that prepared by dispersing, adsorbing or bonding a lipolytic enzyme (lipase) in or to a carrier in an aqueous system and drying the resulting mixture at an adequately slow initial drying rate (European Patent Laid Open Application No. 35883). Although the activity is somewhat weak, a cell-bond lipolytic enzyme (exocellular lipolytic enzyme) can also be used without any specific treatment. In any event, the catalyst A is not specified in the present invention and any one which has transesterification activity and the desired selectivity in the dry reaction system can be used. The selectivity of the transesterification reaction is directed to the α-position of the triglyceride which means that no substatial tranesterification occurs at the β-position. Examples of the catalyst A having such selectivity are lipase originating from animals or vegetables such as pancreas lipase and rice bran lipase; lipases originating from microbes such as those originating from *Rhizopus delemar, Rhizopus japonicus, Rhizopus niveus, Asperigillus nigar, Mucor javanicus;* and the like.

The transesterification reaction is carried out at about 20° to 75° C. according to a standard method.

In order to separate the resultants A and B from the reaction mixture, a conventional technique such as distillation, adsorption, fractionation or the like can be employed. Usually, distillation is convenient. The resultant A can be used in the production of a hard butter as such or it is subjected to fractionation to remove a high melting point fraction and/or a low melting point fraction and then used in the production of a hard butter. This fractionation is well known in the art. In general, when a hard butter is produced from the resultant A alone, quality of the hard butter is inversely proportional to yield thereof.

According to the present invention, the resultant B is hydrogenated and the hydrogenated product (material C) is reused as a part of the mixture A. This makes possible to increase yield of a hard butter produced from the resultant A without any deterioration of quality thereof or to improve quality of the hard butter without lowering of yield thereof. When the resultant B is reused as a part of the mixture A without hydrogenation, this effect can hardly be attained. Another effect of reuse of the material C as a part of the mixture A is that the amount of the material B required to produce a desired amount of a hard butter can be remarkably decreased. Still another effect of reuse of the material C as a part of the mixture A is that an inexpensive crude material can be used as the material B and, even if such the crude material is used, the reactivity can be increased by reuse of the material C. Further, still another effect of reuse of the material C as a part of the mixture A is to shorten the reaction time and this effect can be enhanced by reuse of all or a low melting point fraction of the resultant A as a part of the mixture A together with reuse of the material C.

That is, this reuse of the resultant A means that the transesterification reaction of the material A is divided into multiple stages. In each stage, when a refreshed fatty acid source (i.e. the material C) as well as a low melting point fraction of the resultant A are added to the mixture A, the transesterification can be quite efficiently carried out since the reaction time is remarkably shortened and glycerides having the desired composition are again subjected to the reaction to undergo decomposition and synthesis, avoiding loss thereof. This reuse of all or a low melting point fraction of the resultant A as a part of the mixture A is very effective when the fatty acid residues at the α-position of the material A are composed of not less than 35%, particularly, not less than 40% of the fatty acid residue derived from an unsaturated fatty acid having 18 carbon atoms (oleic acid, linoleic acid or linolenic acid). That is, when the degree of unsaturation of the material A is not less than the above, even if the transesterification reaction proceeds to 100% at a time, it is difficult to obtain a hard butter of good quality unless a low melting point fraction is removed from the resultant A. Therefore, the above reuse of all or the low melting point fraction of the resultant A does not add any extra step to the modification of fats and oils. On the contrary, the yield of a hard butter can be increased by such reuse. In a conventional method, a low melting point fraction obtained by fractionation of a glyceride can hardly be used as a material for the production of a hard butter since it contains a low amount of 2-unsaturated fatty acid residue-1,3-di-saturated fatty acid residue ingredient which is useful for a hard butter and a large amount of a material such as a diglyceride which deteriorates the quality of a hard butter. However, according to the present invention, a low melting point fraction of a glyceride can be reused and due to its nature that the fatty acid residue at the 2-position is unsaturated and thus can be positively utilized in the production of a hard butter. Moreover, in the present invention, the content of a diglyceride in a hard butter can be remarkably decreased by carrying out the transesterification reaction in as dry a state as possible.

Before hydrogenation of the resultant B, if necessary, removal of a hydrogenation catalyst poison and refining of the resultant B may be effected. Hydrogenation can be carried out according to a standard method. The degree of hydrogenation is preferably such that at least 40% of the unsaturated fatty acid residues at the position where the transesterification reaction occurs in the resultant B (the degree of unsaturation can be expressed by iodine value (I.V.)) are saturated by hydrogenation and, most preferably, hydrogenation is carried out until the so-called fully hardened state is obtained (in general, I.V. < 1). When the degrees of hydrogenation becomes higher, more effective results can be attained in the above-mentioned improvement of quality and yield of a hard butter, the reduction of the amount of the material B to be required for transesterification of the material A and the shortening of the reaction time can be obtained.

In another preferred aspect of the present invention, a fraction of a fatty acid having not more than 16 carbon atoms or an ester thereof is removed from the resultant B or the material C before the reuse of the material C. This operation can be carried out together with separation of the resultants A and B from the reaction mixture in single step (rectification). This aspect is useful when the fatty acid residues at the position where the transesterification occurs in the mixture A are mainly composed of those derived from $C_{18}$ and $C_{16}$ fatty acids and, further, the reduction of the content of the fatty acid residues derived from $C_{16}$ fatty acid is required in view of the fatty acid composition of a hard butter to be obtained. By this aspect, the effect of hydrogenation of the resultant B is enhanced. That is, when this aspect is incorporated into the above basic method of the present invention, the improvement of quality and yield of a hard butter, the reduction of the amount of the material B to be required for transesterification of the material A and for the production of a desired amount of a hard butter and the reduction of the reaction time are more efficiently accomplished. Nowadays, since resources being rich in POP are more abundant and inexpensive than those being rich in SOS, in order to obtain a hard butter being rich in POS, it is advantageous to use the resources being rich in POP rather than those being rich in SOS. Further, in the production of high-purity SOS or POP which can be used as an improver of physical properties such as adjustment of a melting point of cacao butter or a hard butter, it is advantageous to obtain SOS. Therefore, this aspect is particularly effective when the fatty acid residues at the α-position of material A are composed of not less than 50% of the fatty acid residue derived from a saturated fatty acid having not more than 16 carbon atoms.

Still another preferred aspect of the present invention is that the catalyst A is dipped in an ester before it is used. This can be effected, for example, by reuse the catalyst B as a part or all of the catalyst A. That is, although the control of water content in the transesterification reaction system is very important as mentioned above, when a catalyst (i.e. enzyme) is freshly prepared, most of water in the reaction system is derived from the catalyst. On the other hand, the removal of water from an enzyme by heat-drying is limited due to inactivation thereof and hence, usually, 1 to several % of water remains in the enzyme. The present inventors have previously found that when an enzyme is used repeatedly, the water content thereof decreases (European Patent Laid Open Application No. 35883). This means that water content of an enzyme can be decreased by dipping it in an oil and hence, quality of a hard butter can be improved. Therefore, the reuse of the catalyst B is useful to reduce the water content of the transesterification reaction system. In this case, generally, only the water content of the substrates (i.e. the materials A and B) should be taken into consideration and a hard butter of good quality can be obtained when water content of the mixture A is maintained at not more than 0.05%.

In the method of the present invention, the ratio of the material A to the material B in the mixture A is generally 1:0.2 to 5. However, the total amount of the fatty acid source (i.e. the material B) required for the transesterification reaction is very small due to reuse of the material C.

The following Examples further illustrate the present invention in detail but are not to be construed to limit the scope thereof. In the examples, all the "parts" and "%'s" are by weight unless otherwise stated.

EXAMPLE 1

A commercially available lipase originating from *Rhizopus japonicus* (1.5 parts) was dissolved in cold water (5 parts) and diatomaceous earth (2.5 parts) was added to the solution with stirring. The resulting mixture was slowly dried at 20° C. under the reduced pressure to give an enzyme preparation containing 1.8% of water.

A middle melting point fraction of palm oil (iodine value (I.V.)35, 11% of unsaturated fatty acid residue and 77% of palmitic acid residue at the α-position) (100 parts) and methyl stearate (purity 901 %, I.V. 0.5) (100 parts) were mixed and the mixture was dried under a reduced pressure to give a substrate containing 0.01 % of water.

The above-obtained enzyme preparation (10 parts) was added to the substrate (200 parts) and the mixture was stirred at 45° C. for 4 days with prevention of water absorption. After removal of the enzyme preparation, the mixture was subjected to rectification to give a triglyceride fraction, a $C_{16}$ methyl ester fraction (purity of $C_{16}$ 90%) and a $C_{18}$ methyl ester fraction (purity of $C_{18}$ 90%). The $C_{18}$ fraction was hydrogenated (hardened) until the I.V. became not more than 1 and thereto was added fresh methyl stearate in such an amount that the resulting mixture became the same amount as that of methyl stearate initially used. The resulting mixture was again mixed with the fresh middle melting point fraction of palm oil in the ratio of 1:1 by weight to give another substrate. By using the resulting substrate and the fresh enzyme preparation, the same run was repeated. A high melting point portion was removed from the triglyceride fraction obtained in each run by solvent fractionation to give a hard butter. For comparison, the same run was repeated except that the $C_{18}$ fraction was not hydrogenated. The I.V. of the methyl ester fraction recovered from each run is shown in Table 1.

TABLE 1

| Runs | Present invention I.V. | Comparative run I.V. |
|---|---|---|
| 1st | 3.8 | 3.9 |
| 2nd | 4.3 | 6.1 |
| 5th | 4.2 | 9.8 |

Every hard butter obtained in each run according to the present invention was similar to cacao butter and showed good results in a chocolate test. However, in the comparative runs, when the fifth run was carried out in order to obtain a hard butter being similar to cacao butter, both high melting and low melting portions had to be removed from the resulting triglyceride fraction which resulated in lowering of yield since, after removal of only the high melting portion from the triglyceride fraction, the resultant had a low melting point (30.7° C., in case of present invention 33.5° C.).

Besides, in order to transesterify the total amount of the middle melting point fraction of palm oil used in the 5 runs (500 parts) at once, 500 parts of methyl stearate was required in a conventional transesterification method. On the contrary, according to the present invention wherein $C_{18}$ methyl ester fraction was recovered after transesterification reaction, hydrogenated and reused, only about 260 parts of methyl stearate, including operational losses, was required.

The hard butter obtained in the 5th run of the present invention had the melting point of 33.5° C. and I.V. of 35. The fatty acid composition thereof is shown in Table 2.

TABLE 2

| Fatty acid composition | $C_{14}$ | $C_{16}$ | $C_{18}$ | $C_{18:1}$ | $C_{18:2}$ |
|---|---|---|---|---|---|
| % | 0.5 | 28.1 | 33.9 | 34.9 | 2.6 |

EXAMPLE 2

The same procedure as described in Example 1 was repeated except that an enzyme preparation was prepared by using a commercially available lipase originated from *Rhizopus niveus* and perlite; stearic acid was substituted for methyl stearate; the reaction was carried out at 69° C. for 4 days; and separation of fatty acid fractions was effected by using a silica gel column. A hard butter similar to cacao butter was constantly obtained in each run.

EXAMPLE 3

A commercially available lipase originating from *Rhizopus niveus* (10 parts) was dissolved in cold water (40 parts) and Celite 545 (diatomaceous earch produced by Johns Manville Sales Corp., U.S.A.) (25 parts) was added to the solution with stirring. The resulting mixture was slowly dried at 15° C. to give an enzyme preparation containing 2.5% of water.

Refined shea butter (I.V. 58, 32% of unsaturated fatty acid residue and 60% of stearic acid residue at α-position) (25 parts) and stearic acid (containing 5.7% of palmitic acid and 2.1% of arachidic acid) (75 parts) were mixed and the mixture was dried at 105° C. under a reduced pressure. Hexane (400 parts) was added to the dried mixture to give a substrate containing 0.01% of water.

The above-obtained enzyme preparation (10 parts) was mixed with the substrate (200 parts) and the mixture was stirred at 45° C. for 2 hours. The enzyme preparation was recovered from the reaction mixture. The recovered enzyme preparation was mixed with the fresh substrate (500 parts) and the transesterification reaction was carried out at 45° C. with prevention of water absorption.

After the reaction, hexane was distilled off from the reaction mixture and fatty acids were recovered from the reaction mixture by distillation. The fatty acids were hydrogenated until a fully hardened state was attained. The hydrogenated fatty acids were mixed with fresh refined shea fat (25 parts) and the transesterification reaction was repeated.

On the other hand, after removal of the fatty acids, the reaction mixture was subjected to fractionation to obtain a liquid-side fraction.

The transesterification reaction time and yield and melting point of the resulting liquid-side fraction are shown in Table 3.

TABLE 3

| | | Liquid-side fraction | |
|---|---|---|---|
| Runs | Reaction time | Yield | Melting point |
| 1st | 96 hours | 94% | 38.5° C. |
| 2nd | 72 hours | 95% | 38.9° C. |

When the liquid-side fraction was mixed with a middle melting point fraction of palm oil in the ratio of 1:1, a hard butter of good quality could be obtained.

EXAMPLE 4

A commercially available lipase originating from *Rhizopus japonicus* (cell-bond enzyme) was dried under a reduced pressure until water content thereof became 1.5%.

A middle melting point fraction of palm oil (I.V. 34) (35 parts), a liquid-side fractionated oil of shea fat (I.V. 67, 37% of unsaturated fatty acid residue and 33% of palmitic acid residue at α-position) (65 parts) and fatty acid methyl ester (60% of stearic acid and 40% of palmitic acid) (200 parts) were mixed to give a substrate containing 0.01% of water. The above enzyme (9 parts) was added to the substrate (300 parts) and the mixture was stirred at 45° C. for 7 days in a closed system. After recovery of the reaction mixture, a methyl ester fraction was separated by distillation and hydrogenated until I.V. thereof became less than 1. The hydrogenated ester fraction was again mixed with the triglyceride fraction recovered from the above reaction mixture and then the resulting mixture was again subjected to the transesterification reaction by using the enzyme recovered from the reaction mixture of the 1st run. After reaction, the substrate was recovered and a methyl ester fraction was removed therefrom. Further, a high melting point fraction was removed from the resulting mixture by solvent fractionation to obtain a hard butter. The hard butter thus obtained was similar to cacao butter in respect of the fatty acid composition and the melting point thereof. The methyl esters removed from the substrate can be further reused in the transesterification after hydrogenation thereof.

EXAMPLE 5

A commercially available pancreas lipase (5 g), polyvinyl alcohol cyanogenated with cyanogen bromide (2 g) and 0.1 M phosphate buffer (pH 7.5) (50 ml) were mixed and the mixture was allowed to stand in a refrigerator overnight. The mixture was filtered and dried under a reduced pressure to give a polyvinyl alcohol immobilized enzyme preparation (water content 1.7%).

Olive oil (81% of unsaturated fatty acid residue at α-position) (100 parts) and ethyl stearate (100 parts) were mixed and the mixture was dried under a reduced pressure to give a substrate (water content 0.015%).

The above-obtained enzyme preparation (7.5 parts) was added to the substrate and the mixture was stirred at 45° C. for 3 days. The substrate was recovered and subjected to distillation to give an ethyl ester fraction and a triglyceride fraction. The ethyl ester fraction was hydrogenated (I.V. 0.5) and mixed with the triglyceride fraction. The mixture was again subjected to the transesterification reaction. After reaction, the substrate was recovered and treated as described above. This procedure was repeated 3 times and the resulting triglyceride fraction was separated into a solid-side fraction and a liquid-side fraction by solvent fractionation. The solid-side fraction had the melting point of 36.5° C. and I.V. of 36. The fatty acid composition thereof is shown in Table 4.

TABLE 4

| Fatty acid composition | $C_{16}$ | $C_{18}$ | $C_{18:1}$ | $C_{18:2}$ | $C_{20}$ |
|---|---|---|---|---|---|
| % | 10.5 | 49.2 | 38.1 | 1.2 | 0.3 |

When this fraction was mixed with a middle melting point fraction of palm oil in the ratio of 1:1, a cacao butter substitute having excellent properties could be obtained.

EXAMPLE 6

A commercially available lipase originating from *Rhizopus delemar* (1 part) and diatomaceous earth (2 parts) were mixed and an appropriate amount of cold water was scattered thereon with stirring to form granules. The granules were dried at 15° C. under a reduced pressure to give an enzyme preparation containing 1.5% of water.

Refined safflower oil (high oleic) (89% of unsaturated fatty acid residue at the α-position) (100 parts) and methyl stearate (purity 93%) (100 parts) were mixed and the mixture was dried under a reduced pressure to give a substrate (water content 0.01%).

The above-obtained enzyme preparation (10 parts) was added to the substrate and the mixture was stirred at 45° C. for 5 days in a closed system. The substrate was recovered and a methyl ester fraction was distilled off therefrom. The resulting triglyceride fraction was separated into a solid-side fraction and a liquid-side fraction by solvent fractionation.

The methyl ester fraction removed from the substrate was hydrogenated until a fully hardened state was attained and thereto was added fresh methyl stearate in such an amount that the resulting ester mixture became 100 parts.

The ester mixture was added to a mixture of the above-obtained liquid side fraction (60 parts) and fresh refined safflower oil (40 parts) to give a substrate. The substrate was again subjected to the transesterification as described above. This procedure was repeated. I.V. of the methyl ester fraction recovered from each run as well as diglyceride content and yield of the high melting point portion of the triglyceride fraction obtained in each run are shown in Table 5.

TABLE 5

| | | Triglyceride fraction | |
|---|---|---|---|
| Runs | Methyl ester fraction I.V. | Diglyceride content (%) | Yield of high melting point portion (%) |
| 1st | 39.2 | 4.5 | 35 |
| 2nd | 30.1 | 5.2 | 40 |
| 3rd | 30.6 | 4.8 | 42 |
| 4th | 31.2 | 5.0 | 45 |
| 5th | 30.2 | 4.9 | 45 |

The high melting point portion of the triglyceride fraction obtained in 5th run could be used as a hard butter as such. In order to further improve quality thereof, an extremely high melting point portion and a liquid-side portion were removed therefrom to obtain a middle melting point portion. This portion had the melting point of 38.0° C. and I.V. of 33 and showed excellent properties for a hard butter. The fatty acid composition is shown in Table 6.

TABLE 6

| Fatty acid composition | $C_{16}$ | $C_{18}$ | $C_{18:1}$ | $C_{18:2}$ | $C_{20}$ |
|---|---|---|---|---|---|
| % | 4.0 | 59.3 | 31.5 | 3.5 | 1.1 |

When this portion was mixed with an equal amount of a middle melting point fraction of palm oil, a hard butter of good quality useful in the chocolate production could be also obtained.

EXAMPLE 7

When the same procedure as described in Example 6 was repeated except that water (0.3%) was added to each run, diglyceride contents in the reaction mixtures of the 1st and 2nd runs were 10.3% and 14.5%, respectively.

What is claimed is:

1. In a method for the modification of a fat or oil by selectively transesterifying:

a mixture, designated as mixture A, which mixture comprises: a glyceride-type fat or oil to be modified, designated as material A and a fatty acid or a monohydric alcohol ester thereof, designated as material B, in the presence of an enzyme catalyst having a selective transesterification activity, designated as catalyst A; and recovering the modified fat or oil designated as resultant A, fatty acid or monohydric alcohol ester thereof reaction residues, designated as resultant B and enzyme catalyst, designated as catalyst B, from the reaction mixture; and then producing a hard butter from the resultant A, the improvement which comprises hydrogenating a part or all the resultant B and reusing the thus hydrogenated product, designated as material C, as a part of the mixture A.

2. The method according to claim 1, wherein the material A contains not less than about 70% of oleic acid residue at the β-position thereof and fatty acid residues being within the shaded part of the accompanying FIG. 1 at the α-position thereof and the selectivity of the transesterification is directed to the α-position of the material A.

3. The method according to claim 1, wherein water content of the transesterification reaction system is not more than 0.18% based on the mixture A.

4. The method according to claim 1, wherein the catalyst A is previously treated by dipping it in a fatty ester.

5. The method according to claim 4, wherein all or a part of the catalyst B is reused as all or a part of the catalyst A.

6. The method according to claim 5, wherein water content of the mixture A is not more than 0.05%.

7. The method according to claim 1, wherein the material A contains not less than 35% of an unsaturated fatty acid residue at the α-position thereof.

8. The method according to claim 7, wherein all of the resultant A or a low-melting point fraction of the resultant A is reused as a part of the mixture A.

9. The method according to claim 1, wherein the material A contains not less than 50% of a fatty acid residue having not more than 16 carbon atoms at the α-position thereof.

10. The method according to claim 9, wherein a fatty acid having not more than 16 carbon atoms or an ester thereof is removed from the resultant B or the material C.

* * * * *